United States Patent
Qiu (10) Patent No.: US 10,980,285 B2
(45) Date of Patent: Apr. 20, 2021

(54) ELECTRONIC CIGARETTE AND CONTROL METHOD THEREOF

(71) Applicants: CHANGZHOU JWEI INTELLIGENT TECHNOLOGY CO., LTD., Jiangsu (CN); JOYETECH EUROPE HOLDING GMBH, Zug (CH)

(72) Inventor: Weihua Qiu, Changzhou (CN)

(73) Assignee: JOYETECH EUROPE HOLDING GMBH, Zug (CH)

(\*) Notice: Subject to any disclaimer, the term of this patent is extended or adjusted under 35 U.S.C. 154(b) by 245 days.

(21) Appl. No.: 16/333,117

(22) PCT Filed: Sep. 13, 2017

(86) PCT No.: PCT/CN2017/101622
§ 371 (c)(1),
(2) Date: Mar. 13, 2019

(87) PCT Pub. No.: WO2018/050072
PCT Pub. Date: Mar. 22, 2018

(65) Prior Publication Data
US 2019/0223507 A1    Jul. 25, 2019

(30) Foreign Application Priority Data

Sep. 13, 2016 (CN) .......................... 201610821818.9

(51) Int. Cl.
*A24F 47/00* (2020.01)
*A61M 15/06* (2006.01)
(Continued)

(52) U.S. Cl.
CPC .......... *A24F 47/008* (2013.01); *A61M 15/06* (2013.01); *A61M 11/042* (2014.02); *A61M 15/0021* (2014.02)

(58) Field of Classification Search
CPC .......................... A24F 47/008; A61M 11/042
(Continued)

(56) References Cited

U.S. PATENT DOCUMENTS 9,022,039 B2 * 5/2015 Hearn .................. A61M 16/20
                                              131/273
10,285,449 B2 * 5/2019 Murison ............... A61M 15/06
(Continued)

FOREIGN PATENT DOCUMENTS

CN        1541577 A      11/2004
CN     201491721 U       6/2010
(Continued)

*Primary Examiner* — Neil Abrams
(74) *Attorney, Agent, or Firm* — Cheng-Ju Chiang (57) ABSTRACT

An electronic cigarette and a control method therefor are provided. The electronic cigarette includes: an atomizing chamber and a cigarette liquid reservoir, configured for storing cigarette liquid; an electric pump, configured for pumping the cigarette liquid in the atomizing chamber to the cigarette liquid reservoir, and for pumping the cigarette liquid in the cigarette liquid reservoir to the atomizing chamber; and a control board electrically connected to the electric pump, the control board being configured to control an operation of the electric pump. By using the electronic cigarette and the control method for the electronic cigarette, the cigarette liquid can be controlled and the liquid leakage can be prevented.

20 Claims, 2 Drawing Sheets

(51) Int. Cl.
*A61M 11/04* (2006.01)
*A61M 15/00* (2006.01)

(58) Field of Classification Search
USPC .................................................. 329/329, 330
See application file for complete search history.

(56) References Cited

U.S. PATENT DOCUMENTS

| | | | |
|---|---|---|---|
| 10,390,563 B2* | 8/2019 | Hawes | H05B 3/0014 |
| 2015/0245654 A1* | 9/2015 | Memari | H02J 7/35 |
| | | | 141/2 |
| 2015/0272216 A1 | 10/2015 | Dai et al. | |
| 2016/0213065 A1* | 7/2016 | Wensley | A24F 40/46 |
| 2018/0279688 A1* | 10/2018 | Qiu | A24F 40/85 |
| 2019/0223507 A1* | 7/2019 | Qiu | A24F 47/008 |
| 2020/0068949 A1* | 3/2020 | Rasmussen | H05B 1/0297 |

FOREIGN PATENT DOCUMENTS

| | | |
|---|---|---|
| CN | 103230100 A | 8/2013 |
| CN | 103932404 A | 7/2014 |
| CN | 204048045 U | 12/2014 |
| CN | 104568954 A | 4/2015 |
| CN | 104736005 A | 6/2015 |
| CN | 204426700 A | 7/2015 |
| CN | 204763415 U | 11/2015 |
| CN | 105212280 A | 1/2016 |
| CN | 204969464 U | 1/2016 |
| CN | 205305989 U | 6/2016 |
| CN | 105901775 A | 8/2016 |
| CN | 106388002 A | 2/2017 |
| JP | H11-33097 A | 2/1999 |

\* cited by examiner

ELECTRONIC CIGARETTE AND CONTROL METHOD THEREOF

CROSS REFERENCE TO RELATED APPLICATION

This application is a 35 U.S.C. § 371 National Phase conversion of International (PCT) Patent Application No. PCT/CN2017/101622, filed on Sep. 13, 2017, which claims the priority of Chinese Patent Application No. 201610821818.9, filed on Sep. 13, 2016. The contents of the above-identified applications are incorporated herein by reference. The PCT International Patent Application was filed and published in Chinese.

TECHNICAL FIELD

The present invention relates to electronic cigarettes, and more particularly to an electronic cigarette and a control method for the control of the cigarette liquid.

BACKGROUND

The electronic cigarette is an electronic product that simulates cigarettes. It converts the cigarette liquid into smoke by means of atomization or the like for the user to inhale. However, the atomizer of the existing electronic cigarettes has a liquid leakage after it is not used for a long time. The main reason for the liquid leakage is: a porous liquid storage material is provided in the atomizing head of the atomizer for liquid isolation purpose, but the cigarette liquid stored in the atomizing chamber of the atomizer will continuously move in the form of molecules and pass through the porous liquid storage material to penetrate into the atomizing head, so that the cigarette liquid stored in the atomizing chamber leaks into the air passage inside the atomizing head after being stored for a long time, which affects the use of the electronic cigarette and reduces the service life of the electronic cigarette.

Therefore, it is necessary to design an electronic cigarette that can reduce the leakage of cigarette liquid and a control method therefor.

SUMMARY

In view of the problems existing in the prior art, the object of the invention is to provide an electronic cigarette and a control method therefor, which can realize the control of the cigarette liquid, and can effectively reduce the leakage of the cigarette liquid.

In order to achieve the above object, a first aspect of the invention provides an electronic cigarette, the electronic cigarette including:

an atomizing chamber and a cigarette liquid reservoir, configured for storing cigarette liquid;

an electric pump, configured for pumping the cigarette liquid in the atomizing chamber to the cigarette liquid reservoir, and for pumping the cigarette liquid in the cigarette liquid reservoir to the atomizing chamber; and a control board electrically connected to the electric pump, the control board being configured to control an operation of the electric pump.

In one embodiment, the control board is further configured to:

after the electronic cigarette is turned on, control the electric pump to pump the cigarette liquid in the cigarette liquid reservoir to the atomizing chamber;

control a liquid level detecting unit to detect the liquid level of the atomizing chamber; and control the electric pump to stop pumping the cigarette liquid in the cigarette liquid reservoir to the atomizing chamber when the detected liquid level reaches a preset liquid level value.

In one embodiment, the control board is further configured to:

after the electronic cigarette stops atomizing the cigarette liquid, determine whether the time of stopping sucking reaches a preset liquid returning time value;

when the time of stopping sucking reaches the preset liquid returning time value, control the electric pump to pump the cigarette liquid in the atomizing chamber to the cigarette liquid reservoir.

In one embodiment, the control board is further configured to:

after the electronic cigarette is turned on, control a liquid level detecting unit to detect whether the liquid level of the atomizing chamber is lower than a preset value;

when the liquid level in the atomizing chamber is lower than the preset value, control the electric pump to pump the cigarette liquid in the cigarette liquid reservoir to the atomizing chamber;

when the liquid level in the atomizing chamber is not lower than the preset value, send out a prompt message to prompt the user whether to pump the cigarette liquid in the cigarette liquid reservoir into the atomizing chamber;

after the prompt message is sent out, if an instruction to stop the electric pump is not received, control the electric pump to pump the cigarette liquid in the cigarette liquid reservoir to the atomizing chamber; if an instruction to stop the electric pump is received, control the electric pump not to operate.

In one embodiment, the electronic cigarette further includes:

an air pressure detecting unit and a pressure relief valve connected to the control board;

the control board is further configured to:

when the cigarette liquid in the cigarette liquid reservoir is pumped into the atomizing chamber, control the air pressure detecting unit to detect the air pressure of the atomizing chamber and determine whether the detected air pressure reaches a preset pressure value;

when the detected air pressure reaches the preset pressure value, control the pressure relief valve to open to relieve pressure.

In one embodiment, the electronic cigarette further includes:

an atomizing head, configured to atomize the cigarette liquid in the atomizing chamber into smoke for the user to suck; and a mouthpiece, configured to be sucked by the user in order for the user to inhale the smoke from the electronic cigarette; and the control board is further configured to:

after the cigarette liquid in the cigarette liquid reservoir is stopped from being pumped to the atomizing chamber, control the atomizing head to atomize the cigarette liquid of the atomizing chamber into smoke for the user to suck through the mouthpiece when the user inhales.

A second aspect of the present invention provides a method for controlling an electronic cigarette, the method including the following steps:

after the electronic cigarette is turned on, pumping the cigarette liquid in the cigarette liquid reservoir to the atomizing chamber;

detecting the liquid level of the atomizing chamber; and stopping pumping the cigarette liquid in the cigarette liquid reservoir to the atomizing chamber when the detected liquid level reaches a preset liquid level value;

after the electronic cigarette stops atomizing the cigarette liquid, pumping the cigarette liquid in the atomizing chamber to the cigarette liquid reservoir.

In one embodiment, the method further includes the following steps:

after the electronic cigarette stops atomizing the cigarette liquid, determining whether the time of stopping sucking reaches a preset liquid returning time value;

when the time of stopping sucking reaches the preset liquid returning time value, pumping the cigarette liquid in the atomizing chamber to the cigarette liquid reservoir.

In one embodiment, after the electronic cigarette is turned on, the method further includes the following steps:

detecting whether the liquid level in the atomizing chamber is lower than a preset value;

when the liquid level in the atomizing chamber is lower than the preset value, pumping the cigarette liquid in the cigarette liquid reservoir to the atomizing chamber;

when the liquid level in the atomizing chamber is not lower than the preset value, sending out a prompt message to prompt the user whether to pump the cigarette liquid in the cigarette liquid reservoir to the atomizing chamber.

In one embodiment, when the cigarette liquid in the cigarette liquid reservoir is pumped into the atomizing chamber, the method further includes the following steps:

detecting an air pressure of the atomizing chamber and determining whether the detected air pressure reaches a preset pressure value;

when the detected air pressure reaches the preset pressure value, depressurizing the atomizing chamber.

A third aspect of the present invention provides an electronic cigarette, the electronic cigarette includes:

a cigarette liquid reservoir, configured for storing cigarette liquid;

a control unit connected to a liquid conveying device, the control unit being configured to control the liquid conveying device to convey the cigarette liquid in an atomizing chamber to the cigarette liquid reservoir after electronic cigarette stops atomizing the cigarette liquid.

In one embodiment, the control unit is further configured to determine whether the time of stopping sucking reaches a preset liquid returning time value;

when the time of stopping sucking reaches the preset liquid returning time value, the control unit controls the liquid conveying device to convey the cigarette liquid in the atomizing chamber to the cigarette liquid reservoir.

In one embodiment, the liquid conveying device is further configured to convey the cigarette liquid in the cigarette liquid reservoir to the atomizing chamber.

In one embodiment, further including a liquid level detecting unit connected to the control unit, wherein the control unit is further configured to control the liquid level detecting unit to detect the liquid level in the atomizing chamber, and when the detected liquid level reaches a preset liquid level value, to control the liquid conveying device to stop conveying the cigarette liquid in the cigarette liquid reservoir to the atomizing chamber.

In one embodiment, further including a liquid level detecting unit connected to the control unit, wherein the control unit is further configured to control the liquid level detecting unit to detect the liquid level in the atomizing chamber and determine whether the detected liquid level is lower than a preset value, and when the liquid level is lower than the preset value, to control the liquid conveying device to convey the cigarette liquid in the cigarette liquid reservoir to the atomizing chamber.

In one embodiment, the control unit is further configured to, when the liquid level detected by the liquid level detecting unit is not lower than the preset value, send out a prompt message to prompt the user whether to convey the cigarette liquid in the cigarette liquid reservoir to the atomizing chamber.

In one embodiment, further including:

an air pressure detecting unit and a pressure relief valve connected to the control unit;

the control unit is further configured to:

when the liquid conveying device conveys the cigarette liquid in the cigarette liquid reservoir to the atomizing chamber, control the air pressure detecting unit to detect an air pressure of the atomizing chamber and determine whether the detected air pressure reaches a preset pressure value;

when the detected air pressure reaches the preset pressure value, control the pressure relief valve to open to relieve pressure.

A fourth aspect of the present invention provides a method for controlling an electronic cigarette, the method including:

after the electronic cigarette stops atomizing the cigarette liquid, conveying the cigarette liquid in the atomizing chamber to the cigarette liquid reservoir.

In one embodiment, the method further includes:

determining, after the electronic cigarette stops atomizing the cigarette liquid, whether the time of stopping sucking reaches a preset liquid returning time value;

when the time of stopping sucking reaches the preset liquid returning time value, conveying the cigarette liquid in the atomizing chamber to the cigarette liquid reservoir.

In one embodiment, the method further includes the following steps:

after the electronic cigarette is turned on, conveying the cigarette liquid in the cigarette liquid reservoir to the atomizing chamber;

detecting the liquid level of the atomizing chamber; and stopping conveying the cigarette liquid in the cigarette liquid reservoir to the atomizing chamber when the detected liquid level reaches a preset liquid level value.

In one embodiment, the method further includes:

detecting and determining whether a liquid level of the atomizing chamber is lower than a preset value;

when the liquid level is lower than the preset value, conveying the cigarette liquid in the cigarette liquid reservoir to the atomizing chamber.

In one embodiment, the method further includes:

when the liquid level is not lower than the preset value, sending out a prompt message to prompt the user whether to convey the cigarette liquid in the cigarette liquid reservoir to the atomizing chamber.

In one embodiment, the method further includes:

after the prompt message is sent out, if an instruction to stop the liquid conveying device is not received, controlling the liquid conveying device to convey the cigarette liquid in the cigarette liquid reservoir to the atomizing chamber; if an instruction to stop the liquid conveying device is received, controlling the liquid conveying device not to operate.

In one embodiment, when the cigarette liquid in the cigarette liquid reservoir is conveyed into the atomizing chamber, the method further includes the following steps:

detecting an air pressure of the atomizing chamber and determining whether the detected air pressure reaches a preset pressure value;

when the detected air pressure reaches the preset pressure value, depressurizing the atomizing chamber.

In one embodiment, the method further includes:

when the liquid level of the atomizing chamber is lower than a preset value, stopping conveying the cigarette liquid in the atomizing chamber to the cigarette liquid reservoir.

By using the electronic cigarette and the control method for electronic cigarette of the invention, the cigarette liquid in the atomizing chamber can be pumped into the cigarette liquid reservoir by the electric pump when the atomizing chamber needs to be evacuated, so that when the atomizing chamber is not in use for a long time, the cigarette liquid in the atomizing chamber can be pumped into the cigarette liquid reservoir. When not in use for a long time, since there is no cigarette liquid in the atomizing chamber, the leakage phenomenon of the cigarette liquid is effectively reduced, to prolong the service life of the electronic cigarette.

REFERENCE SIGNS

| electronic cigarette | 100 |
| --- | --- |
| atomizing chamber | 1 |
| cigarette liquid reservoir | 2 |
| liquid conveying device | 3 |
| control board | 4 |
| power source | 5 |
| casing | 6 |
| mouthpiece | 7 |
| pressure relief valve | 8 |
| liquid level detecting unit | 9, 90, 91 |
| first liquid level detecting unit | 90 |
| second liquid level detecting unit | 91 |
| atomizing head | 10 |
| display screen | 11 |
| air pressure detecting unit | 12 |

The invention will be further illustrated by the following detailed description in conjunction with the accompanying drawings.

DETAILED DESCRIPTION OF EMBODIMENTS

The present invention will be described in detail below in conjunction with the embodiments shown in the drawings. However, the embodiments are not intended to limit the present invention, and structural or functional changes made by those skilled in the art based on these embodiments are included in the scope of the present invention.

Figure 1:
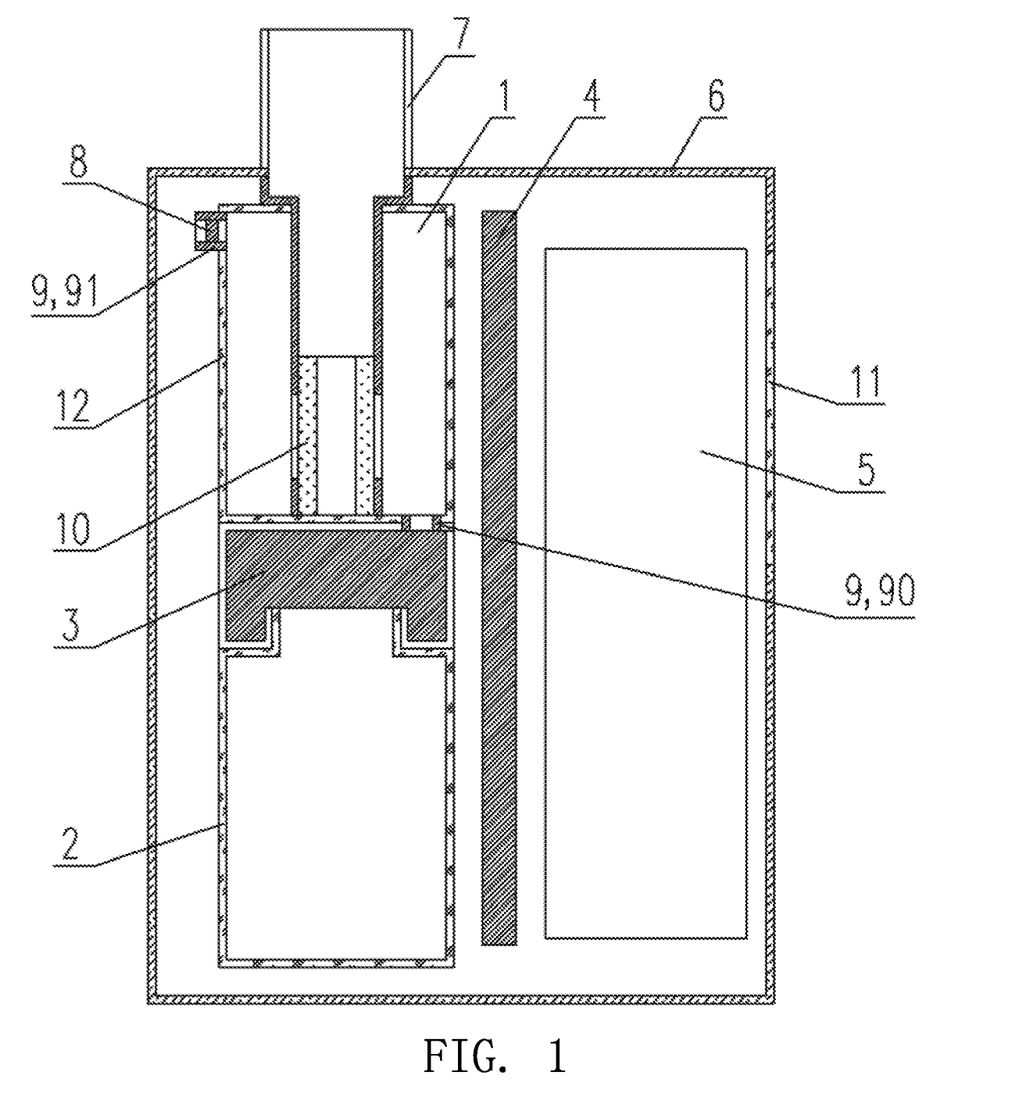
FIG. 1 is a schematic structural diagram of an electronic cigarette according to a preferred embodiment of the present invention.

FIG. 1 is a schematic structural diagram of an electronic cigarette according to an embodiment of the present invention. The electronic cigarette can realize control to the cigarette liquid.

The electronic cigarette 100 includes an atomizing chamber 1, a cigarette liquid reservoir 2, an electric pump 3, a control board 4, a power source 5, a casing 6, a mouthpiece 7, a pressure relief valve 8, a liquid level detecting unit 9, an atomizing head 10, a display screen 11, and an air pressure detecting unit 12.

It is understood that the electronic cigarette 100 realizes the conveyance of the cigarette liquid between the atomizing chamber 1 and the cigarette liquid reservoir 2 by using a liquid conveying device. In one embodiment, the liquid conveying device is used for conveying the cigarette liquid in the atomizing chamber 1 to the cigarette liquid reservoir 2. In one embodiment, the liquid conveying device is used for conveying the cigarette liquid in the cigarette liquid reservoir 2 to the atomizing chamber 1.

In this embodiment, the liquid conveying device is an electrically driven liquid conveying device, specifically, an electric pump. The electric pump 3 can pump the cigarette liquid in the atomizing chamber 1 to the cigarette liquid reservoir 2 or pump the cigarette liquid in the cigarette liquid reservoir 2 to the atomizing chamber 1.

It is understood that the electronic cigarette 100 is provided with a control unit electrically connected to the liquid conveying device, the power source 5, the pressure relief valve 8, the liquid level detecting unit 9, the atomizing head 10, the display screen 11 and the air pressure detecting unit 12, respectively. The control unit is configured to control the conveying operation of the liquid conveying device, and is also used to control the power source 5, the pressure relief valve 8, the liquid level detecting unit 9, the atomizing head 10, the display screen 11 and the air pressure detecting unit 12 to operate. In this embodiment, the control unit is a control board 4. In other embodiments, the control unit may also be an electronic device having control function, such as a control chip or a control circuit.

In this embodiment, the cigarette liquid reservoir 2 is used for storing the cigarette liquid, and the atomizing chamber 1 may also store a portion of the cigarette liquid. The atomizing chamber 1 is provided and fixed in the casing 6. The atomizing chamber 1 and the cigarette liquid reservoir 2 are each connected to the electric pump 3. Optionally, the cigarette liquid reservoir 2 can be detached freely, and can be covered with a sealing cover after being detached, so as to store the cigarette liquid for a long time. When the cigarette liquid reservoir 2 is covered and sealed by the sealing cover, the cigarette liquid does not easily come into contact with the air, so that it is not easily deteriorated.

The electric pump 3 is used to pump the cigarette liquid in the atomizing chamber 1 to the cigarette liquid reservoir 2 or to pump the cigarette liquid in the cigarette liquid reservoir 2 to the atomizing chamber 1. Specifically, the control board 4 is electrically connected to the electric pump 3, for controlling the electric pump 3 to pump the cigarette liquid in the atomizing chamber 1 to the cigarette liquid reservoir 2 when the cigarette liquid in the atomizing chamber 1 needs to be evacuated, or for controlling the electric pump 3 to pump the cigarette liquid in the cigarette liquid reservoir 2 to the atomizing chamber 1 when the cigarette liquid needs to be injected into the atomizing chamber 1. The power source 5 is electrically connected to electronic components in the electronic cigarette 100 for providing energy for the electronic components in the electronic cigarette 100, wherein the electronic components include, but are not limited to, the electric pump 3, the control board 4, the pressure relief valve 8, the liquid level detecting unit 9, the atomizing head 10, the display screen 11, the air pressure detecting unit 12, etc.

The atomizing head 10 is electrically connected to the control board 4, and the atomizing head 10 is configured to atomize the cigarette liquid in the atomizing chamber 1 into smoke for the user to suck. The mouthpiece 7 can be sucked by the user, in order for the user to inhale the smoke from the electronic cigarette 100.

The air pressure detecting unit 12 and the pressure relief valve 8 are disposed on the wall of the atomizing chamber 1 and electrically connected to the control board 4. Further, the pressure relief valve 8 is disposed through the wall of the atomizing chamber 1, and the air pressure detecting unit 12 is disposed on an inner wall of the atomizing chamber 1. The air pressure detecting unit 12 is configured to detect the air pressure of the atomizing chamber 1, and when the detected air pressure of the atomizing chamber 1 reaches a preset pressure value, the pressure relief valve 8 is opened to depressurize the atomizing chamber 1.

The liquid level detecting unit 9 is electrically connected to the control board 4, and the liquid level detecting unit 9 is configured to detect the liquid level of the atomizing chamber 1. In this embodiment, the liquid level detecting unit 9 may include a first liquid level detecting unit 90 disposed at the bottom surface of the atomizing chamber 1 and/or a second liquid level detecting unit 91 disposed at an upper end of the atomizing chamber 1 (e.g., at the position where the pressure relief valve 8 is located). The liquid level detecting unit 90 is configured to detect a lowest liquid level of the atomizing chamber 1 to determine whether there is liquid in the atomizing chamber 1. The liquid level detecting unit 91 is configured to detect a highest liquid level of the atomizing chamber 1 to determine whether to stop injecting liquid into the atomizing chamber 1. In this embodiment, the first liquid level detecting unit 90 and the second liquid level detecting unit 91 may be liquid level meter of a tuning fork vibrating type, a pressure type, an ultrasonic type and the like.

In other embodiments, the liquid level detecting unit 90 may also be disposed at a lower end of the atomizing chamber 1, and the position of the liquid level detecting unit 90 at the lower end is determined according to a preset evacuation liquid level for evacuating the atomizing chamber 1. The preset evacuation liquid level is defined to be the liquid level that the atomizing chamber 1 needs to be evacuated. For example, the preset evacuation liquid level may be the liquid level corresponding to 10% of the maximum liquid level of the atomizing chamber 1, and when the liquid level of the atomizing chamber 1 reaches 10% of the maximum liquid level of the atomizing chamber 1, the atomizing chamber 1 is required to be evacuated. The liquid level detecting unit 90 is set at the lower end of the atomizing chamber 1 so that it can detect whether the preset evacuation liquid level is reached.

In other embodiments, the liquid level detecting unit 90 may also include a plurality of liquid level detecting elements (not shown) disposed at various positions along the atomizing chamber 1 to detect the liquid level of the atomizing chamber 1 in real time.

The display screen 11 is disposed on the casing 6 and electrically connected to the control board 4 for displaying prompt message or parameter information of the electronic cigarette, for example, prompting the user to evacuate the atomizing chamber 1 or to inject liquid into the atomizing chamber 1. The parameter information of the electronic cigarette may include power supply voltage, real-time current, power being set, real-time resistance value, and the like.

After the electronic cigarette 100 is turned on, the control board 4 is configured to control the cigarette liquid in the cigarette liquid reservoir 2 to be pumped into the atomizing chamber 1 according to the actual needs. In this embodiment, after the electronic cigarette 100 is turned on, the control board 4 is also configured to control the liquid level detecting unit 90 to detect whether the liquid level of the atomizing chamber 1 is lower than a preset value, to determine whether there is liquid in the atomizing chamber 1. It is understood that, when the detected liquid level is lower than the preset value, it is determined that there is no liquid in the atomizing chamber 1; when the detected liquid level is higher than the preset value, it is determined that there is liquid in the atomizing chamber 1. The preset value refers to a liquid height value that is preset in the control unit. Optionally, the preset value is 0.1-5 mm. Further, the preset value is 1 mm, 2 mm, or 3 mm.

When there is no cigarette liquid in the atomizing chamber 1, the control board 4 controls the electric pump 3 to pump the cigarette liquid from the cigarette liquid reservoir 2 into the atomizing chamber 1, so that the atomizing chamber 1 is filled with cigarette liquid. When there is cigarette liquid in the atomizing chamber 1, the control board 4 sends a prompt message to the display screen 11 to prompt the user not to convey the cigarette liquid in the cigarette liquid reservoir 2 to the atomizing chamber 1. The electronic cigarette 100 may further be provided with a vibration unit (not shown) to prompt the user not to convey the cigarette liquid in the cigarette liquid reservoir 2 to the atomizing chamber 1. A confirmation window can also be displayed on the display screen 11 for the user to confirm whether to ignore the prompt message. After the prompt message is sent, the control unit determines whether an instruction to stop the operation of the liquid conveying device is received. In this embodiment, the control board 4 determines whether there is an instruction to stop the operation of the electric pump 3. If the user ignores the prompt message, that is, when the control unit does not receive an instruction to stop the operation of the liquid conveying device, the liquid conveying device operates to convey the cigarette liquid in the cigarette liquid reservoir 2 to the atomizing chamber 1. In this embodiment, when the control board 4 does not receive an instruction to stop the operation of the electric pump, the electric pump 3 pumps the cigarette liquid in the cigarette liquid reservoir 2 to the atomizing chamber 1. If the user gives an instruction without ignoring the prompt message, for example, by pressing a button or pressing the touch panel on the display screen 11, the control unit will receive an instruction to stop the operation of the liquid conveying device, and the control unit controls the liquid conveying device not to operate. In this embodiment, the electronic cigarette 100 will receive an instruction to stop the operation of the electric pump, and the control board 4 controls the electric pump 3 not to operate. By prompting the user that it is not needed to convey the cigarette liquid in the cigarette liquid reservoir 2 to the atomizing chamber 1, the cigarette liquid is no longer conveyed to the atomizing chamber 1 when there is cigarette liquid in the atomizing chamber 1, thereby preventing excessive cigarette liquid in the atomizing chamber 1 to affect the suction experience, also reducing the operation steps of the liquid conveying device and reducing the energy loss.

The control board 4 is further configured to control the liquid level detecting unit 9 to detect the liquid level of the atomizing chamber 1 and determine whether the detected liquid level reaches a preset liquid level value. In this embodiment, the liquid level detecting unit 91 is used to detect whether the liquid level of the atomizing chamber 1 reaches the preset liquid level value. When the detected liquid level reaches the preset liquid level value, the control board 4 controls the electric pump 3 to stop pumping the cigarette liquid in the cigarette liquid reservoir 2 to the atomizing chamber 1, i.e., stopping the liquid injection operation. When the detected liquid level does not reach the preset liquid level value, the control board 4 continues to control the electric pump 3 to pump the cigarette liquid in the cigarette liquid reservoir 2 to the atomizing chamber 1. The preset liquid level value may be preset by the user, e.g., equaling to the maximum liquid level of the atomizing chamber 1 or 70% to 90% of the maximum liquid level of the atomizing chamber 1. The preset liquid level value can also be set according to the output power of the electronic cigarette 100. The installation position of the liquid level detecting unit 91 on the atomizing chamber 1 is set according to the preset liquid level value.

In one embodiment, the preset liquid level value is set according to the output power of the electronic cigarette 100, and the output power has a corresponding relationship with the preset liquid level value. For example, the larger the output power, the larger the preset liquid level value. Further, the output power is a continuous range value, and each range value corresponds to a preset liquid level value. For example, when the output power is 1-10 W, the preset liquid level value is 10% of the volume of the atomizing chamber 1; when the output power is 10-20 W, the preset liquid level value is 20% of the volume of the atomizing chamber 1; and when the output power is 20-30 W, the preset liquid level value is 30% of the volume of the atomizing chamber 1, etc. The correspondence between the output power and the preset liquid level value can be stored previously in the control board 4, and the control board 4 adjusts the preset liquid level value according to the output power.

In this embodiment, when the cigarette liquid in the cigarette liquid reservoir 2 is pumped into the atomizing chamber 1, the control board 4 is further configured to control the air pressure detecting unit 12 to detect the air pressure of the atomizing chamber 1 and determine whether the detected air pressure reaches a preset pressure value. When the detected air pressure reaches the preset pressure value, the control board 4 controls the pressure relief valve 8 to open to relieve pressure, and when the detected air pressure does not reach the preset pressure value, the control board 4 continues to detect the air pressure of the atomizing chamber 1 and continues to detect whether the liquid level of the atomizing chamber 1 reaches the preset liquid level value. The preset pressure value is preset according to the performance of the atomizing chamber 1.

After the liquid injection operation is stopped, the control board 4 controls the atomizing head 10 to atomize the cigarette liquid of the atomizing chamber 1 into smoke for the user to suck through the mouthpiece 7 when the user inhales.

The control board 4 is further configured to determine whether the time of stopping sucking reaches a preset liquid returning time value after the user stops smoking, that is, after the electronic cigarette 100 stops atomizing the cigarette liquid, and further, that is, after the atomizing head 10 stops atomizing the cigarette liquid. It is understood that the time of stopping sucking refers to the time period when the atomizing head 10 stops atomizing the cigarette liquid to a certain time point. Further, the control unit has a recording time function, and when the atomizing head 10 stops atomizing the cigarette liquid, the control unit starts recording time until a certain time point thereafter. This certain time point is determined by the preset liquid returning time value. The control board 4 controls the electric pump 3 to pump the cigarette liquid in the atomizing chamber 1 to the cigarette liquid reservoir 2 when the time of stopping sucking reaches the preset liquid returning time value. The preset liquid returning time value is used to determine the waiting time for the electronic cigarette 100 to evacuate the cigarette liquid in the atomizing chamber 1. The liquid returning time value is preset according to the evacuating frequency of the user. When the evacuating frequency is high, the preset liquid returning time value is short, and when the evacuating frequency is low, the preset liquid returning time value is long. If the user needs to evacuate the cigarette liquid in the atomizing chamber 1 after using the electronic cigarette 100 every time, the preset liquid returning time value can be set short, for example, 10 minutes, 1 hour, and the like. If the user needs to evacuate the cigarette liquid in the atomizing chamber 1 after the electronic cigarette 100 is not used for a long time, the preset liquid returning time value can be set long, for example, 12 hours, 24 hours, and the like.

In one embodiment, after the user stops smoking, that is, after the electronic cigarette 100 stops atomizing the cigarette liquid, the control unit is further configured to control the cigarette liquid in the atomizing chamber 1 to be conveyed to the cigarette liquid reservoir 2 when an instruction is given by pressing a button or touching the display screen.

In other embodiments, an air pressure detecting unit 12 and a pressure relief valve 8 may be disposed on the wall of the cigarette liquid reservoir 2 for detecting whether the air pressure of the cigarette liquid reservoir 2 reaches a preset pressure value. When the detected air pressure reaches the preset pressure value, the control board 4 controls the pressure relief valve 8 to open to relieve pressure. The preset pressure value is preset according to the performance of the cigarette liquid reservoir 2.

The control board 4 is further configured to control the electronic cigarette 100 to be turned off after the cigarette liquid in the atomizing chamber 1 is evacuated.

Figure 2:
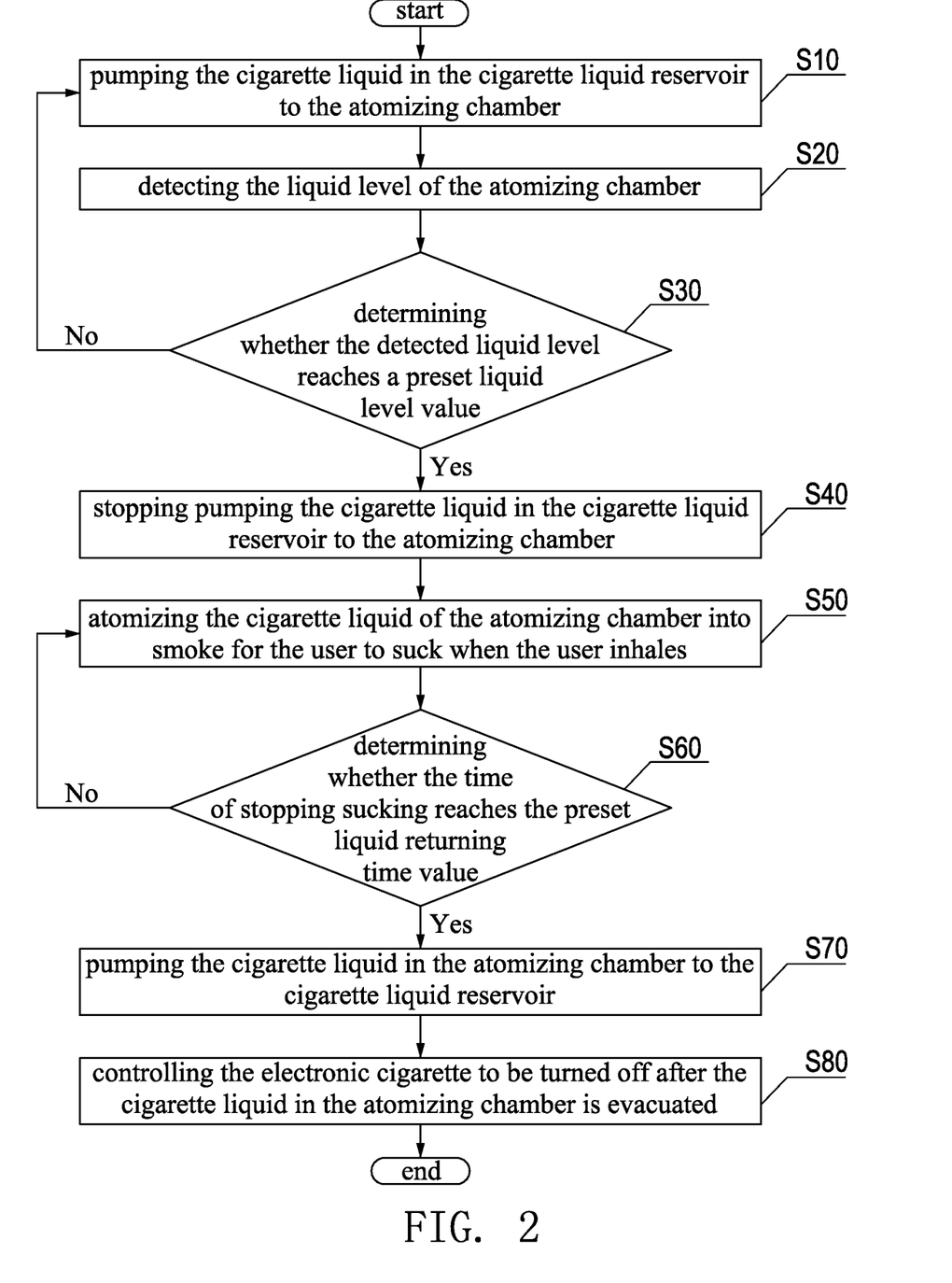
FIG. 2 is a flow chart of a control method for an electronic cigarette according to a preferred embodiment of the present invention.

FIG. 2 is a flow chart showing a method for controlling an electronic cigarette according to a preferred embodiment of the present invention.

In step S10, after the electronic cigarette 100 is turned on, the control board 4 controls the cigarette liquid in the cigarette liquid reservoir 2 to be pumped into the atomizing chamber 1.

In this embodiment, before the step S10, the method may further include the following steps: after the electronic cigarette 100 is turned on, the control board 4 controls the liquid level detecting unit 9 (e.g., the liquid level detecting unit 90) to detect the liquid level of the atomizing chamber 1, to determine whether there is liquid in the atomizing chamber 1. When there is no liquid in the atomizing chamber 1, the control board 4 controls the electric pump 3 to pump the cigarette liquid in the cigarette liquid reservoir 2 to the atomizing chamber 1. When there is liquid in the atomizing chamber 1, the control board 4 sends a prompt message to the display screen 11 to prompt the user whether to convey the cigarette liquid in the cigarette liquid reservoir 2 to the atomizing chamber 1. If the user ignores the prompt message, that is, the control unit does not receive an instruction to stop the operation of the liquid conveying device, the liquid conveying device operates to convey the cigarette liquid in the cigarette liquid reservoir 2 to the atomizing chamber 1. In this embodiment, when the control board 4 does not receive an instruction to stop the operation of the electric pump, the electric pump 3 pumps the cigarette liquid in the cigarette liquid reservoir 2 to the atomizing chamber 1. If the user gives an instruction without ignoring the prompt message, for example, by pressing a button on the display screen 11, the control unit will receive an instruction to stop the operation of the liquid conveying device, and the control unit controls the liquid conveying device not to operate. In this embodiment, the electronic cigarette 100 will receive an instruction to stop the operation of the electric pump, and the control board 4 controls the electric pump 3 not to operate.

In step S20, the control board 4 controls the liquid level detecting unit 9 (e.g., the liquid level detecting unit 91) to detect the liquid level of the atomizing chamber 1.

In step S30, the control board 4 determines whether the detected liquid level reaches a preset liquid level value. When the detected liquid level reaches the preset liquid level value, step S40 is performed, that is, the control board 4 controls the electric pump 3 to stop pumping the cigarette liquid in the cigarette liquid reservoir 2 to the atomizing chamber 1, i.e., stopping the liquid injection operation. When the detected liquid level has not reached the preset liquid level value, the process returns to the step S10, that is, the control board 4 continues to control the electric pump 3 to pump the cigarette liquid in the cigarette liquid reservoir 2 to the atomizing chamber 1. The preset liquid level value may be preset by the user, for example, equaling to the maximum liquid level of the atomizing chamber 1 or 70% to 90% of the maximum liquid level of the atomizing chamber 1. The preset liquid level value can also be set according to the output power of the electronic cigarette 100.

In this embodiment, before the step S30, the method may further include the following steps: the control board 4 controls the air pressure detecting unit 12 to detect the air pressure of the atomizing chamber 1, and determines whether the detected air pressure reaches a preset pressure value. When the detected air pressure reaches the preset pressure value, the control board 4 controls the pressure relief valve 8 to open to depressurize the atomizing chamber 1. When the detected air pressure does not reach the preset pressure value, the control board 4 continues to detect the air pressure of the atomizing chamber 1 and continues to detect whether the liquid level of the atomizing chamber 1 reaches the preset liquid level value. The preset pressure value is preset according to the performance of the atomizing chamber 1. After the pressure is relieved, the cigarette liquid of the cigarette liquid reservoir 2 can be pumped into the atomizing chamber 1 more easily, and the atomizing head 10 is also easy to absorb the cigarette liquid of the atomizing chamber 1, so that the liquid supply is ensured and the suction effect is better.

In step S50, when the user inhales, the control board 4 controls the atomizing head 10 to atomize the cigarette liquid of the atomizing chamber 1 into smoke for the user to suck through the mouthpiece 7.

In step S60, the control board 4 determines whether the time of stopping sucking reaches the preset liquid returning time value. When the time of stopping sucking reaches the preset liquid returning time value, step S70 is performed, that is, the control board 4 controls the electric pump 3 to pump the cigarette liquid in the atomizing chamber 1 to the cigarette liquid reservoir 2. When the time of stopping sucking does not reach the preset liquid returning time value, the process returns to the step S50, that is, when the user inhales, the control board 4 controls the atomizing head 10 to atomize the cigarette liquid of the atomizing chamber 1 into smoke for the user to suck through the mouthpiece 7. The preset liquid returning time value is used to determine the waiting time for the electronic cigarette 100 to evacuate the cigarette liquid in the atomizing chamber 1. The liquid returning time value is preset according to the evacuating frequency of the user. When the evacuating frequency is high, the preset liquid returning time value is short, and when the evacuating frequency is low, the preset liquid returning time value is long. If the user needs to evacuate the cigarette liquid in the atomizing chamber 1 after using the electronic cigarette 100 every time, the preset liquid returning time value can be set short, for example, 10 minutes, 1 hour, and the like. If the user needs to evacuate the cigarette liquid in the atomizing chamber 1 after the electronic cigarette 100 is not used for a long time, the preset liquid returning time value can be set to be long, for example, 12 hours, 24 hours, and the like.

In step S80, after the cigarette liquid in the atomizing chamber 1 is evacuated, the control board 4 controls the electronic cigarette 100 to be turned off.

Optionally, the step of evacuating the cigarette liquid in the atomizing chamber 1 includes: the liquid level detecting unit 9 detects the liquid level of the atomizing chamber 1, when the detected liquid level of the atomizing chamber 1 is lower than a preset value, the cigarette liquid in the atomizing chamber 1 is stopped from being conveyed into the cigarette liquid reservoir 2. The preset value refers to a preset liquid height. Optionally, the preset value is 0.1-5 mm. Further, the preset height value is 1 mm, 2 mm, or 3 mm.

It is understood that the electric pump 3 in the above embodiments can be replaced by a liquid conveying device of other forms. The control board 4 can be replaced by a control unit.

In other embodiments, a method for controlling an electronic cigarette is further provided. The method includes the following steps:

After the electronic cigarette 100 stops atomizing the cigarette liquid, the cigarette liquid in the atomizing chamber 1 is conveyed into the cigarette liquid reservoir 2.

Optionally, the method includes: after the electronic cigarette 100 stops atomizing the cigarette liquid, determining whether the time of stopping sucking reaches a preset liquid returning time value;

When the time of stopping sucking reaches the preset liquid returning time value, the cigarette liquid in the atomizing chamber 1 is conveyed into the cigarette liquid reservoir 2.

Optionally, the method further includes: when the liquid level of the atomizing chamber 1 is lower than a preset height value, stopping conveying the cigarette liquid in the atomizing chamber 1 into the cigarette liquid reservoir 2.

Optionally, the method further includes the following steps: after the electronic cigarette 100 is turned on, the cigarette liquid in the cigarette liquid reservoir 2 is conveyed into the atomizing chamber 1;

Detecting the liquid level of the atomizing chamber 1; and

When the detected liquid level reaches a preset liquid level value, the cigarette liquid in the cigarette liquid reservoir 2 is stopped from being conveyed into the atomizing chamber 1.

Optionally, the method further includes: detecting and determining whether the liquid level of the atomizing chamber 1 is lower than a preset value;

When the liquid level is lower than the preset value, the control unit controls the liquid conveying device to convey the cigarette liquid in the cigarette liquid reservoir 2 into the atomizing chamber 1;

When the liquid level is not lower than the preset value, a prompt message is sent to prompt the user whether to convey the cigarette liquid in the cigarette liquid reservoir 2 to the atomizing chamber 1.

Optionally, after the prompt message is sent, the control unit determines whether an instruction to stop the operation of the liquid conveying device is received, and if not received, the liquid conveying device operates to convey the cigarette liquid in the cigarette liquid reservoir to the cigarette liquid reservoir; if received, the liquid conveying device does not operate. By prompting the user that it is not needed to convey the cigarette liquid in the cigarette liquid reservoir 2 to the atomizing chamber 1, the cigarette liquid is no longer conveyed to the atomizing chamber 1 when there is cigarette liquid in the atomizing chamber 1, thereby preventing excessive cigarette liquid in the atomizing chamber 1 to affect the suction experience, also reducing the operation steps of the liquid conveying device and reducing the energy loss.

Optionally, when the cigarette liquid in the cigarette liquid reservoir 2 is conveyed into the atomizing chamber 1, the following steps are further included:

Detecting an air pressure of the atomizing chamber, and determining whether the detected air pressure reaches a preset pressure value;

When the detected air pressure reaches a preset pressure value, the atomizing chamber is depressurized.

It should be understood that, although the description is described in terms of embodiments, each embodiment contains not only an independent technical solution, such is only for the sake of clarity. Technicians in the field shall take the description as a whole, and the technical solutions in the embodiments may also be combined as appropriate to form other embodiments that can be understood by those skilled in the field.

The detailed descriptions set forth above are merely illustrative of the possible embodiments of the present invention, and are not intended to limit the scope of the present invention. Variations and modifications are intended to fall within the scope of the invention, as long as it is within the spirit of the invention.

What is claimed is:

1. An electronic cigarette comprising:
    an atomizing chamber and a cigarette liquid reservoir, configured for storing cigarette liquid;
    an electric pump, configured for pumping the cigarette liquid in the atomizing chamber to the cigarette liquid reservoir, and for pumping the cigarette liquid in the cigarette liquid reservoir to the atomizing chamber; and
    a control board electrically connected to the electric pump, the control board being configured to control an operation of the electric pump.

2. The electronic cigarette according to claim 1, wherein the control board is further configured to:
    after the electronic cigarette is turned on, control the electric pump to pump the cigarette liquid in the cigarette liquid reservoir to the atomizing chamber;
    control a liquid level detecting unit to detect the liquid level of the atomizing chamber; and
    control the electric pump to stop pumping the cigarette liquid in the cigarette liquid reservoir to the atomizing chamber when the detected liquid level reaches a preset liquid level value.

3. The electronic cigarette according to claim 1, wherein the control board is further configured to:
    after the electronic cigarette stops atomizing the cigarette liquid, determine whether the time of stopping sucking reaches a preset liquid returning time value;
    when the time of stopping sucking reaches the preset liquid returning time value, control the electric pump to pump the cigarette liquid in the atomizing chamber to the cigarette liquid reservoir.

4. The electronic cigarette according to claim 1, wherein the control board is further configured to:
    after the electronic cigarette is turned on, control a liquid level detecting unit to detect whether the liquid level of the atomizing chamber is lower than a preset value;
    when the liquid level in the atomizing chamber is lower than the preset value, control the electric pump to pump the cigarette liquid in the cigarette liquid reservoir to the atomizing chamber;
    when the liquid level in the atomizing chamber is not lower than the preset value, send out a prompt message to prompt the user whether to pump the cigarette liquid in the cigarette liquid reservoir into the atomizing chamber;
    after the prompt message is sent out, if an instruction to stop the electric pump is not received, control the electric pump to pump the cigarette liquid in the cigarette liquid reservoir to the atomizing chamber; if an instruction to stop the electric pump is received, control the electric pump not to operate.

5. The electronic cigarette according to claim 1, wherein the electronic cigarette further comprises:
    an air pressure detecting unit and a pressure relief valve connected to the control board;
    the control board is further configured to:
    when the cigarette liquid in the cigarette liquid reservoir is pumped into the atomizing chamber, control the air pressure detecting unit to detect the air pressure of the atomizing chamber and determine whether the detected air pressure reaches a preset pressure value;
    when the detected air pressure reaches the preset pressure value, control the pressure relief valve to open to relieve pressure.

6. The electronic cigarette according to claim 5, wherein the electronic cigarette further comprises:
    an atomizing head, configured to atomize the cigarette liquid in the atomizing chamber into smoke for the user to suck;
    a mouthpiece, configured to be sucked by the user in order for the user to inhale the smoke from the electronic cigarette; and
    the control board is further configured to:
    after the cigarette liquid in the cigarette liquid reservoir is stopped from being pumped to the atomizing chamber, control the atomizing head to atomize the cigarette liquid of the atomizing chamber into smoke for the user to suck through the mouthpiece when the user inhales.

7. A method for controlling the electronic cigarette according to claim 1, the method comprising the following steps:
    after the electronic cigarette is turned on, pumping the cigarette liquid in the cigarette liquid reservoir to the atomizing chamber;
    detecting the liquid level of the atomizing chamber; and
    stopping pumping the cigarette liquid in the cigarette liquid reservoir to the atomizing chamber when the detected liquid level reaches a preset liquid level value;
    after the electronic cigarette stops atomizing the cigarette liquid, pumping the cigarette liquid in the atomizing chamber to the cigarette liquid reservoir.

8. The method according to claim 7, wherein the method further comprises the following steps:
    after the electronic cigarette stops atomizing the cigarette liquid, determining whether the time of stopping sucking reaches a preset liquid returning time value;

when the time of stopping sucking reaches the preset liquid returning time value, pumping the cigarette liquid in the atomizing chamber to the cigarette liquid reservoir.

9. The method according to claim 7, wherein after the electronic cigarette is turned on, the method further comprises the following steps:
    detecting whether the liquid level in the atomizing chamber is lower than a preset value;
    when the liquid level in the atomizing chamber is lower than the preset value, pumping the cigarette liquid in the cigarette liquid reservoir to the atomizing chamber;
    when the liquid level in the atomizing chamber is not lower than the preset value, sending out a prompt message to prompt the user whether to pump the cigarette liquid in the cigarette liquid reservoir to the atomizing chamber.

10. The method according to claim 7, wherein when the cigarette liquid in the cigarette liquid reservoir is pumped into the atomizing chamber, the method further comprises the following steps:
    detecting an air pressure of the atomizing chamber and determining whether the detected air pressure reaches a preset pressure value;
    when the detected air pressure reaches the preset pressure value, depressurizing the atomizing chamber.

11. An electronic cigarette comprising:
    a cigarette liquid reservoir, configured for storing cigarette liquid;
    a control unit connected to a liquid conveying device, the control unit being configured to control the liquid conveying device to convey the cigarette liquid in an atomizing chamber to the cigarette liquid reservoir after electronic cigarette stops atomizing the cigarette liquid.

12. The electronic cigarette according to claim 11, wherein the control unit is further configured to determine whether the time of stopping sucking reaches a preset liquid returning time value;
    when the time of stopping sucking reaches the preset liquid returning time value, the control unit controls the liquid conveying device to convey the cigarette liquid in the atomizing chamber to the cigarette liquid reservoir.

13. The electronic cigarette according to claim 11, wherein the liquid conveying device is further configured to convey the cigarette liquid in the cigarette liquid reservoir to the atomizing chamber.

14. The electronic cigarette according to claim 13, further comprising a liquid level detecting unit connected to the control unit, wherein the control unit is further configured to control the liquid level detecting unit to detect the liquid level in the atomizing chamber, and when the detected liquid level reaches a preset liquid level value, to control the liquid conveying device to stop conveying the cigarette liquid in the cigarette liquid reservoir to the atomizing chamber.

15. The electronic cigarette according to claim 13, further comprising a liquid level detecting unit connected to the control unit, wherein the control unit is further configured to control the liquid level detecting unit to detect the liquid level in the atomizing chamber and determine whether the detected liquid level is lower than a preset value, and when the liquid level is lower than the preset value, to control the liquid conveying device to convey the cigarette liquid in the cigarette liquid reservoir to the atomizing chamber.

16. The electronic cigarette according to claim 15, wherein the control unit is further configured to, when the liquid level detected by the liquid level detecting unit is not lower than the preset value, send out a prompt message to prompt the user whether to convey the cigarette liquid in the cigarette liquid reservoir to the atomizing chamber.

17. The electronic cigarette according to claim 13, further comprising:
    an air pressure detecting unit and a pressure relief valve connected to the control unit;
    the control unit is further configured to:
    when the liquid conveying device conveys the cigarette liquid in the cigarette liquid reservoir to the atomizing chamber, control the air pressure detecting unit to detect an air pressure of the atomizing chamber and determine whether the detected air pressure reaches a preset pressure value;
    when the detected air pressure reaches the preset pressure value, control the pressure relief valve to open to relieve pressure.

18. A method for controlling the electronic cigarette according to claim 11, the method comprising:
    after the electronic cigarette stops atomizing the cigarette liquid, conveying the cigarette liquid in the atomizing chamber to the cigarette liquid reservoir.

19. The method according to claim 18, wherein the method further comprises:
    determining, after the electronic cigarette stops atomizing the cigarette liquid, whether the time of stopping sucking reaches a preset liquid returning time value;
    when the time of stopping sucking reaches the preset liquid returning time value, conveying the cigarette liquid in the atomizing chamber to the cigarette liquid reservoir.

20. The method according to claim 18, wherein the method further comprises the following steps:
    after the electronic cigarette is turned on, conveying the cigarette liquid in the cigarette liquid reservoir to the atomizing chamber;
    detecting the liquid level of the atomizing chamber; and
    stopping conveying the cigarette liquid in the cigarette liquid reservoir to the atomizing chamber when the detected liquid level reaches a preset liquid level value.

* * * * *